(12) United States Patent
Skarbnik et al.

(10) Patent No.: US 9,131,957 B2
(45) Date of Patent: Sep. 15, 2015

(54) AUTOMATIC TOOL MARKING

(75) Inventors: Nikolay Skarbnik, Yokneam Illit (IL); Adi Navve, Kfar Saba (IL); Shai Finkman, Haifa (IL)

(73) Assignee: GYRUS ACMI, INC., Southborough, MA (US)

( * ) Notice: Subject to any disclaimer, the term of this patent is extended or adjusted under 35 U.S.C. 154(b) by 439 days.

(21) Appl. No.: 13/610,887

(22) Filed: Sep. 12, 2012

(65) Prior Publication Data

US 2014/0074134 A1    Mar. 13, 2014

(51) Int. Cl.
*A61B 17/32* (2006.01)
*A61B 17/34* (2006.01)
*A61M 25/01* (2006.01)
*A61B 19/00* (2006.01)

(52) U.S. Cl.
CPC ............ *A61B 17/3421* (2013.01); *A61B 19/44* (2013.01); *A61B 19/5202* (2013.01); *A61B 19/5244* (2013.01); *A61B 19/54* (2013.01); *A61B 2019/444* (2013.01); *A61B 2019/446* (2013.01); *A61B 2019/4836* (2013.01); *A61B 2019/4857* (2013.01); *A61B 2019/5265* (2013.01); *A61B 2019/545* (2013.01); *A61B 2019/5437* (2013.01); *A61B 2019/5483* (2013.01); *A61M 25/0108* (2013.01)

(58) Field of Classification Search
None
See application file for complete search history.

(56) References Cited

U.S. PATENT DOCUMENTS

| 4,792,252 | A * | 12/1988 | Kremer et al. ............... 401/206 |
| 6,777,623 | B2 | 8/2004 | Ballard |
| 7,557,710 | B2 | 7/2009 | Sanchez et al. |
| 7,795,491 | B2 | 9/2010 | Stewart et al. |
| 2005/0004431 | A1 | 1/2005 | Kogasaka et al. |
| 2007/0197865 | A1 | 8/2007 | Miyake et al. |
| 2007/0265502 | A1 | 11/2007 | Minosawa et al. |
| 2009/0327102 | A1 | 12/2009 | Maniar et al. |
| 2011/0174877 | A1 | 7/2011 | Fleck et al. |
| 2011/0221463 | A1 | 9/2011 | Livneh |
| 2012/0182409 | A1 | 7/2012 | Moriyama et al. |

FOREIGN PATENT DOCUMENTS

| JP | 9028713 A | 2/1997 |
| JP | 2000-166857 A | 6/2000 |
| JP | 2000-245689 A | 9/2000 |
| JP | 2004-041778 A | 2/2004 |

OTHER PUBLICATIONS

Intertronics, "OPTI-TEC Water Soluble Temporary Adhesives", version 1.3, UK, Apr. 2012 (http://www.intertronics.co.uk/products/opt6055.htm).

PCT Application # PCT/US13/56699 International Search Report and Written Opinion dated Nov. 25, 2013.

* cited by examiner

*Primary Examiner* — Gregory Anderson
*Assistant Examiner* — Robert Lynch
(74) *Attorney, Agent, or Firm* — D. Kligler I.P. Services Ltd.

(57) ABSTRACT

Surgical apparatus, including a trocar having a tubular member with a tubular member distal end and a tubular member proximal end. The apparatus further includes a tool having a tool proximal end and a tool distal end. The tool is insertably disposed within the tubular member with the tool distal end projecting beyond the tubular member distal end. The apparatus further includes an indicator indicating the tool distal end while the tool distal end projects beyond the tubular member distal end.

8 Claims, 9 Drawing Sheets

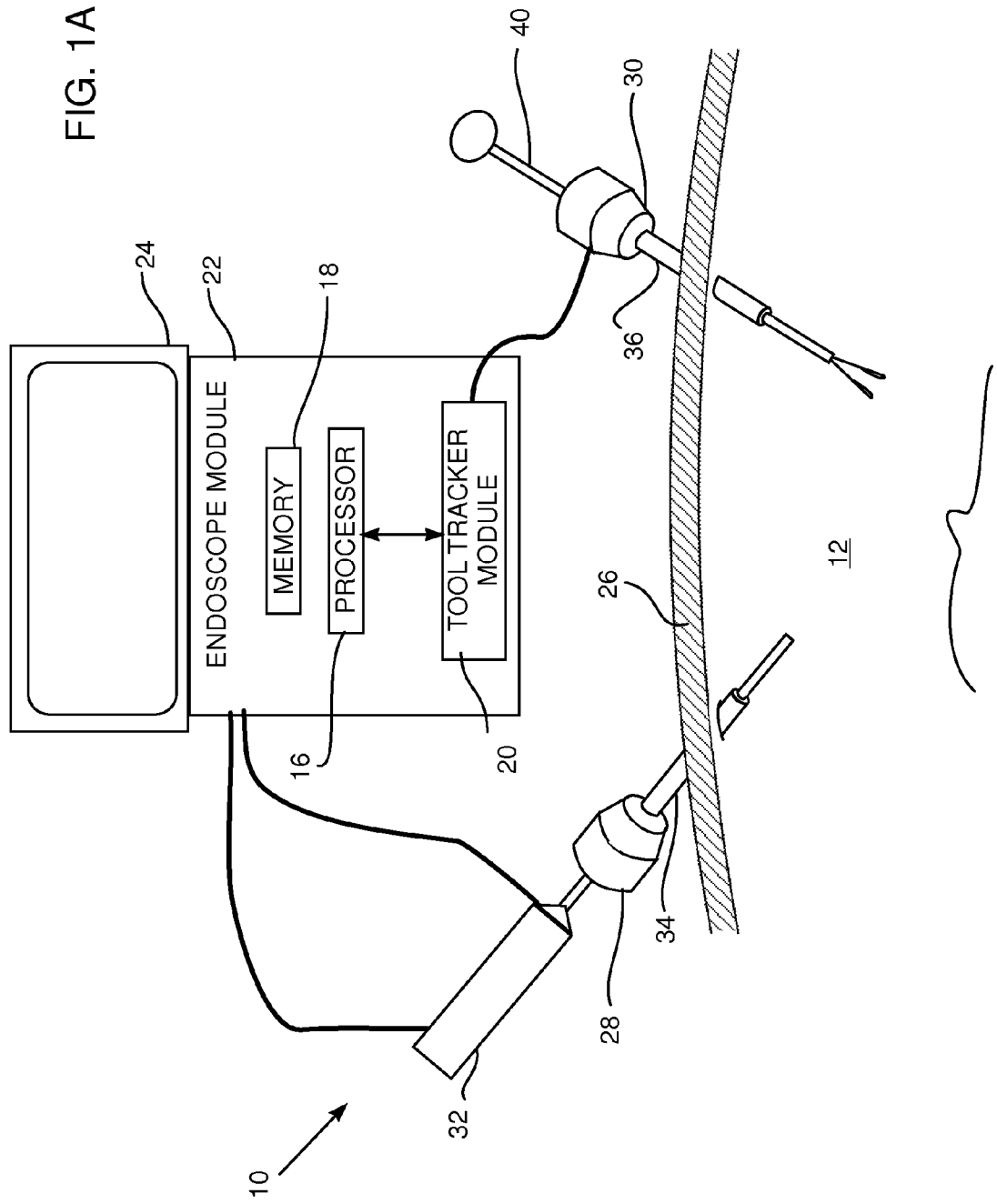

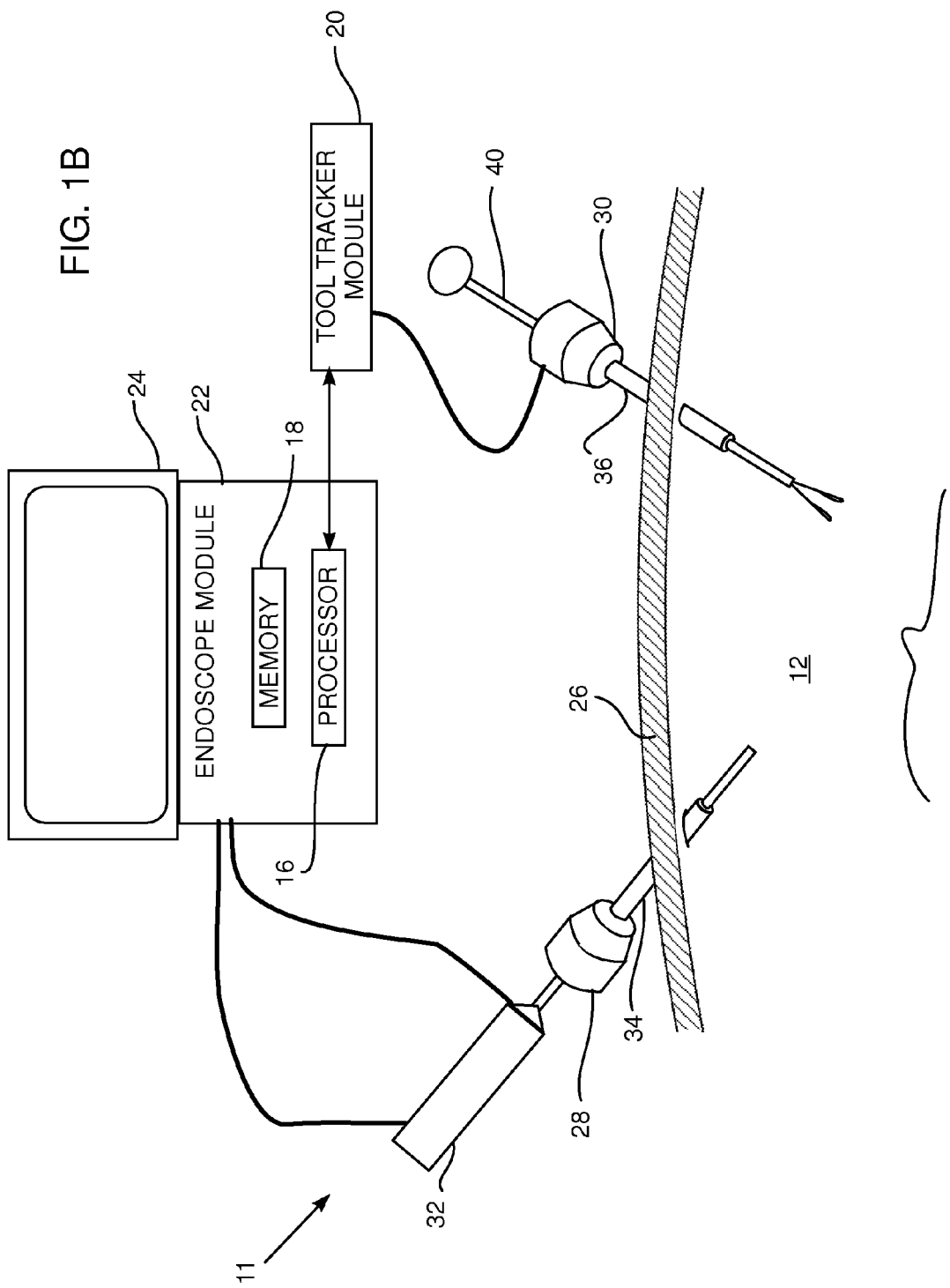

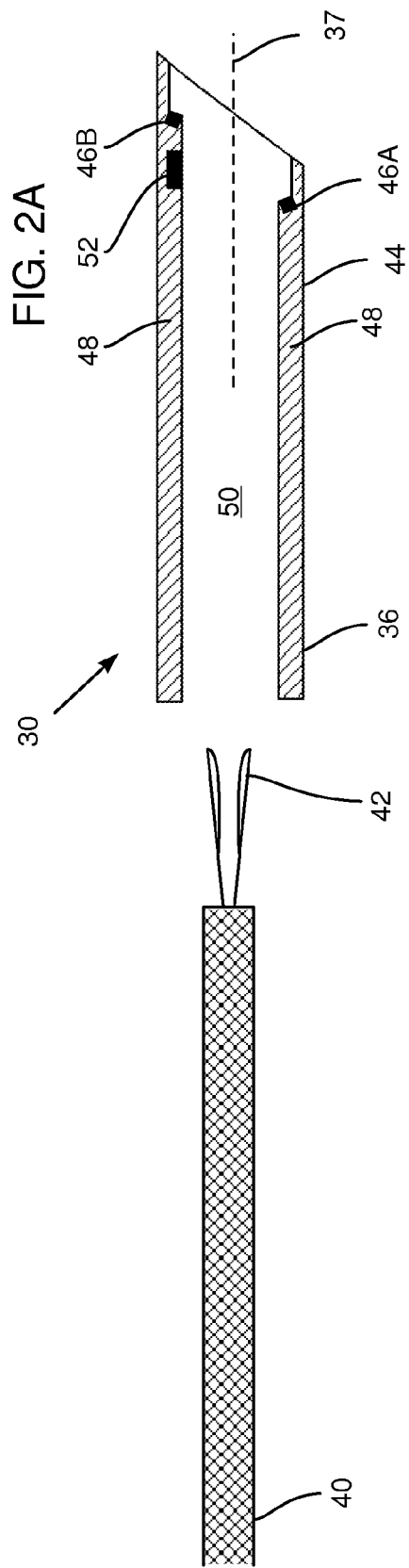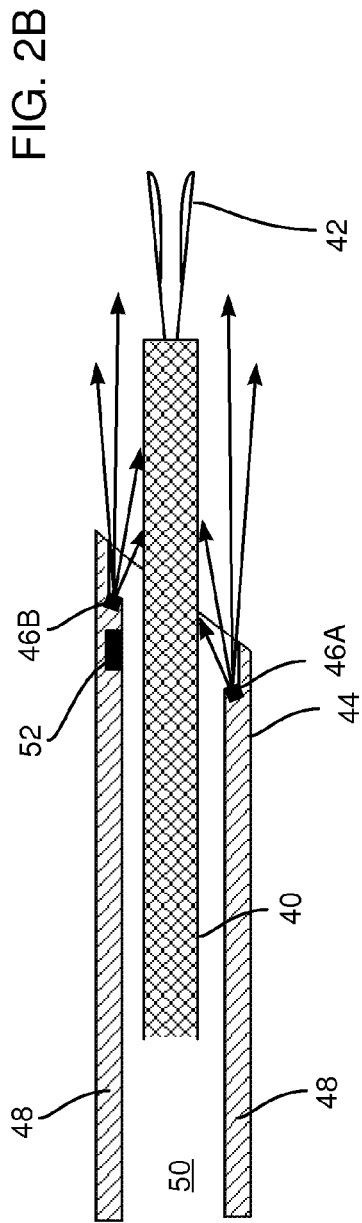

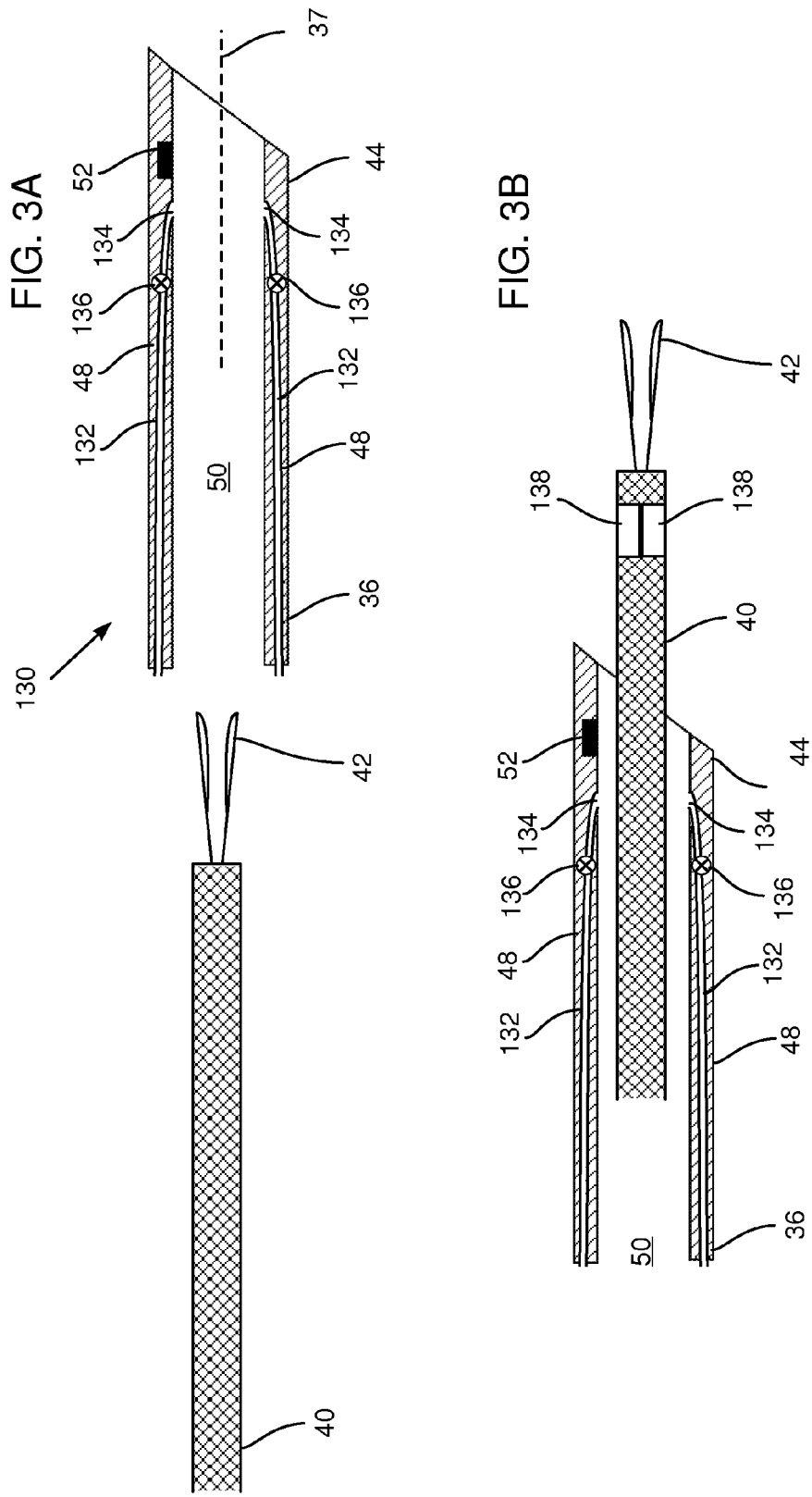

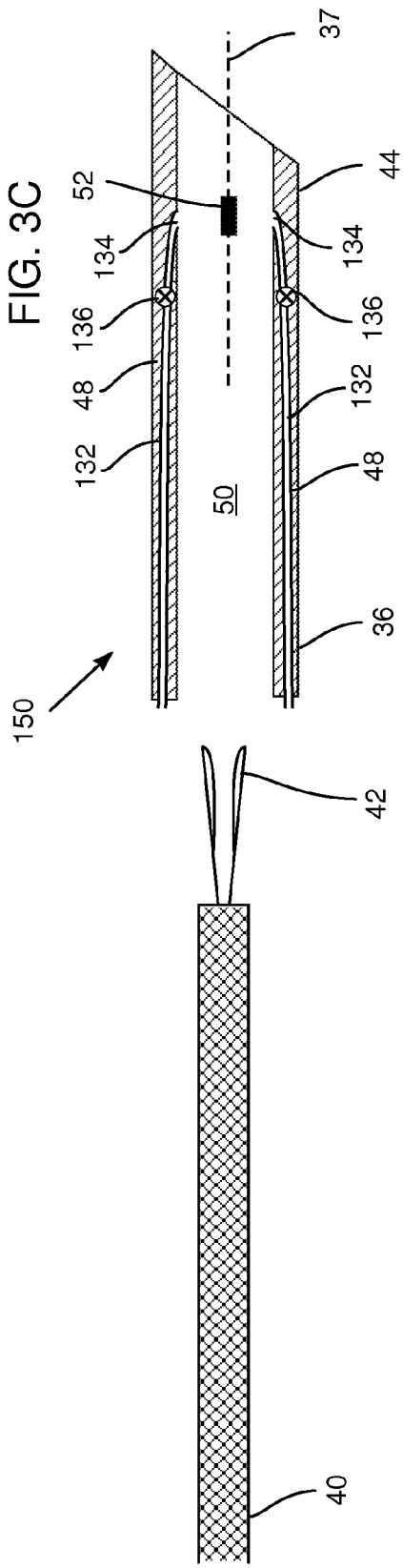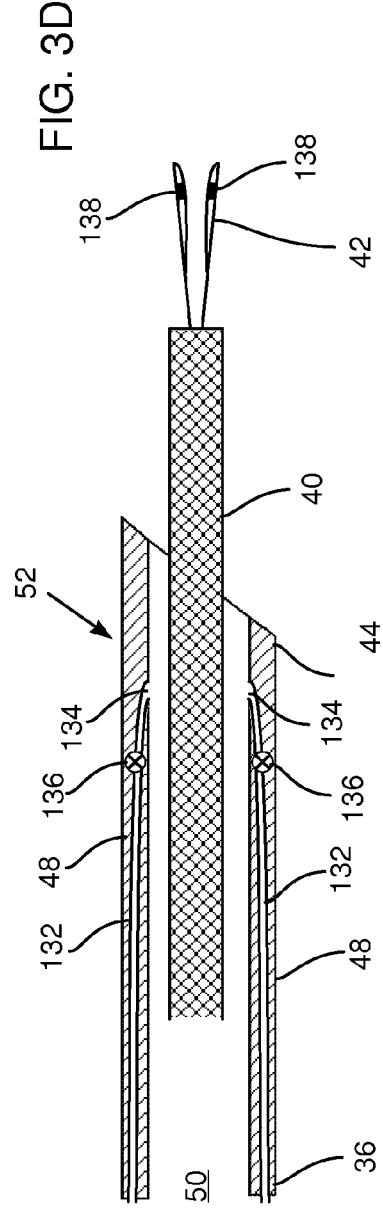

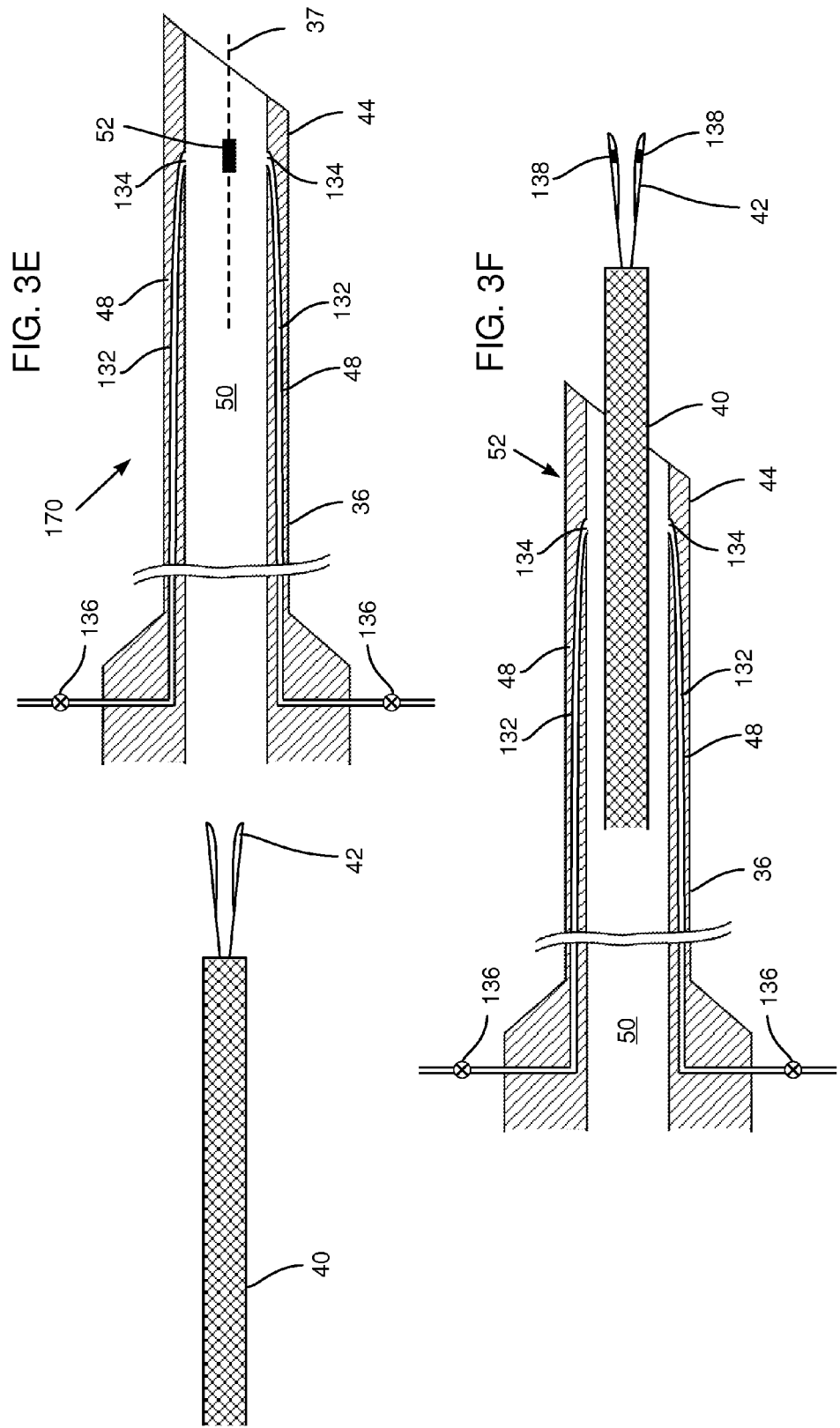

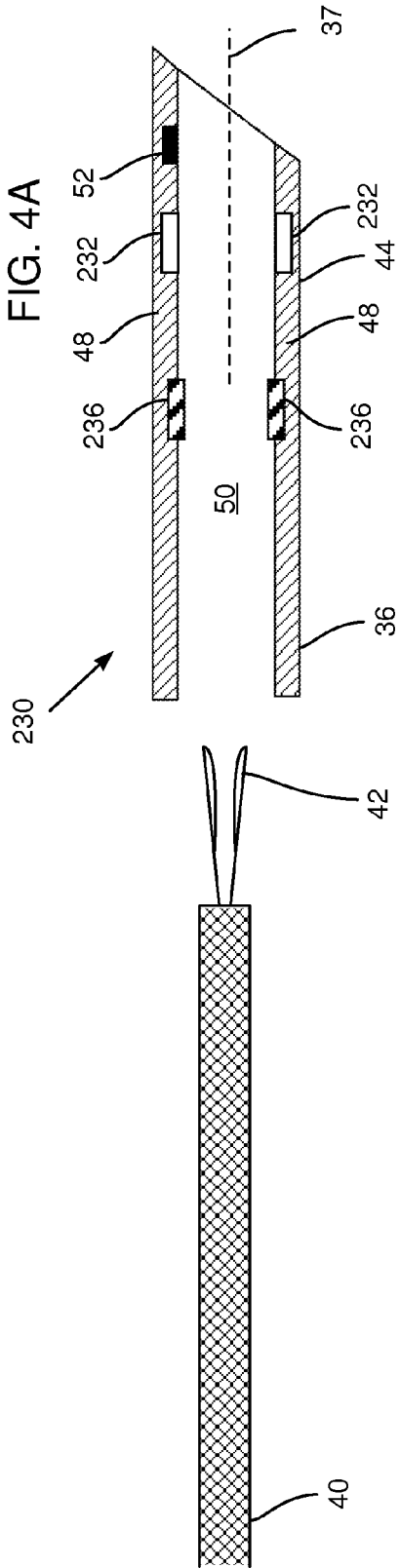
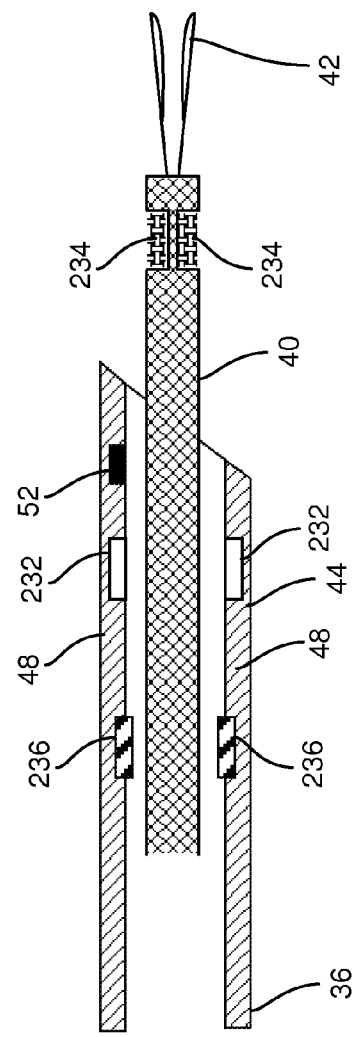
FIG. 4A
FIG. 4B

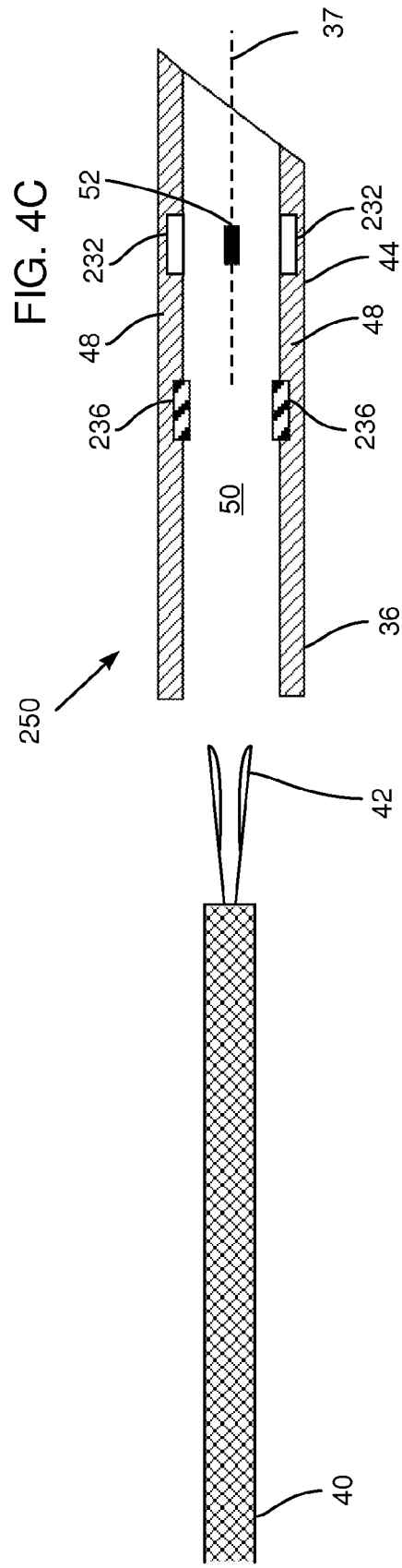
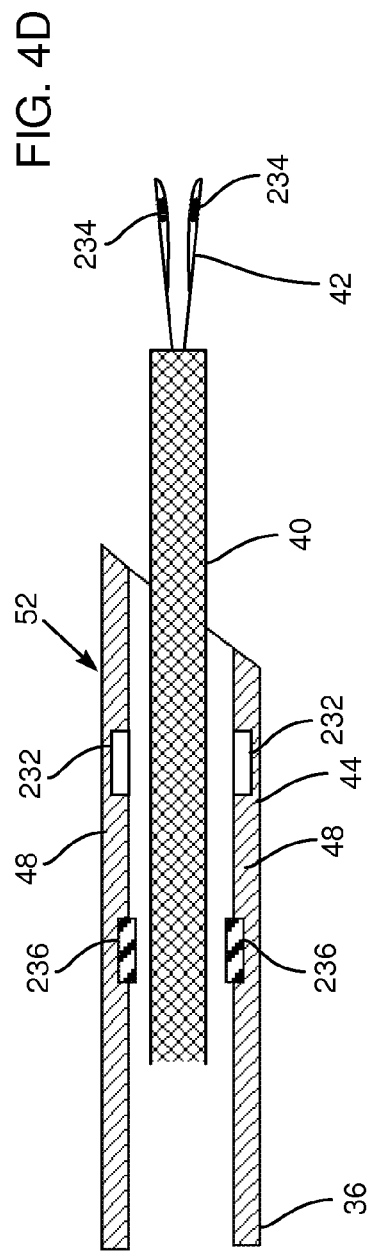

AUTOMATIC TOOL MARKING

FIELD OF THE INVENTION

The present invention relates generally to invasive medical procedures, and specifically to tracking items used during such procedures.

BACKGROUND OF THE INVENTION

Tracking of tools used during an invasive medical procedure, regardless of whether or not the procedure may be classed as minimally invasive, is extremely important. In some cases, the tracking may be performed if the tools have a preset feature, such as a color or shape, and if analysis of an image of the procedure allows the tool to be identified on the basis of the preset feature. However, such a tracking system fails if a tool without the preset feature is used during the procedure.

An improved tool tracking system would therefore be advantageous.

SUMMARY OF THE INVENTION

An embodiment of the present invention provides surgical apparatus including:

a trocar having a tubular member with a tubular member distal end and a tubular member proximal end;

a tool having a tool proximal end and a tool distal end, the tool being insertably disposed within the tubular member with the tool distal end projecting beyond the tubular member distal end; and an indicator indicating the tool distal end while the tool distal end projects beyond the tubular member distal end.

Typically, the apparatus further includes a sensor sensing a position of the tool, and the indicator indicates the tool distal end based on a signal of the sensor. The indicator may be an illuminator disposed on the trocar and configured to illuminate the tool distal end based on the signal. Typically, on illumination the tool distal end generates an illumination spectrum different from a tissue spectrum generated by tissue in proximity to the tool.

In a disclosed embodiment the indicator is an applicator, disposed on the trocar, configured to apply a marker to the tool upon passage of the tool beyond the tubular member distal end.

The marker may consist of a liquid, configured to dry in response to being applied to the tool. Alternatively, the marker consists of a label, configured to be deposited on the tool. The apparatus may include a label remover disposed in the trocar, configured to remove the label after deposition thereof, and upon withdrawal of the tool from the trocar via the tubular member. The label may be configured to be removed from the tool on autoclaving the tool.

In an alternative embodiment, the apparatus includes a processor, configured to track the tool in response to the indication of the indicator.

The present invention will be more fully understood from the following detailed description of the embodiments thereof, taken together with the drawings in which:

BRIEF DESCRIPTION OF THE DRAWINGS

FIG. 1A is a schematic illustration of an automated tool tracking system, according to an embodiment of the present invention;

FIG. 1B is a schematic illustration of an alternative automated tool tracking system, according to an embodiment of the present invention;

FIGS. 2A and 2B are schematic cross-sectional illustrations of a trocar, according to an embodiment of the present invention;

FIGS. 3A and 3B are schematic cross-sectional illustrations of a trocar, according to an alternative embodiment of the present invention;

FIGS. 3C and 3D are schematic cross-sectional illustrations of a trocar, according to a further alternative embodiment of the present invention;

FIGS. 3E and 3F are schematic cross-sectional illustrations of a trocar, according to a yet further embodiment of the present invention;

FIGS. 4A and 4B are schematic cross-sectional illustrations of a trocar, according to another alternative embodiment of the present invention;

FIGS. 4C and 4D are schematic cross-sectional illustrations of a trocar, according to yet another embodiment of the present invention;

DETAILED DESCRIPTION OF EMBODIMENTS

Overview

Figure 5:
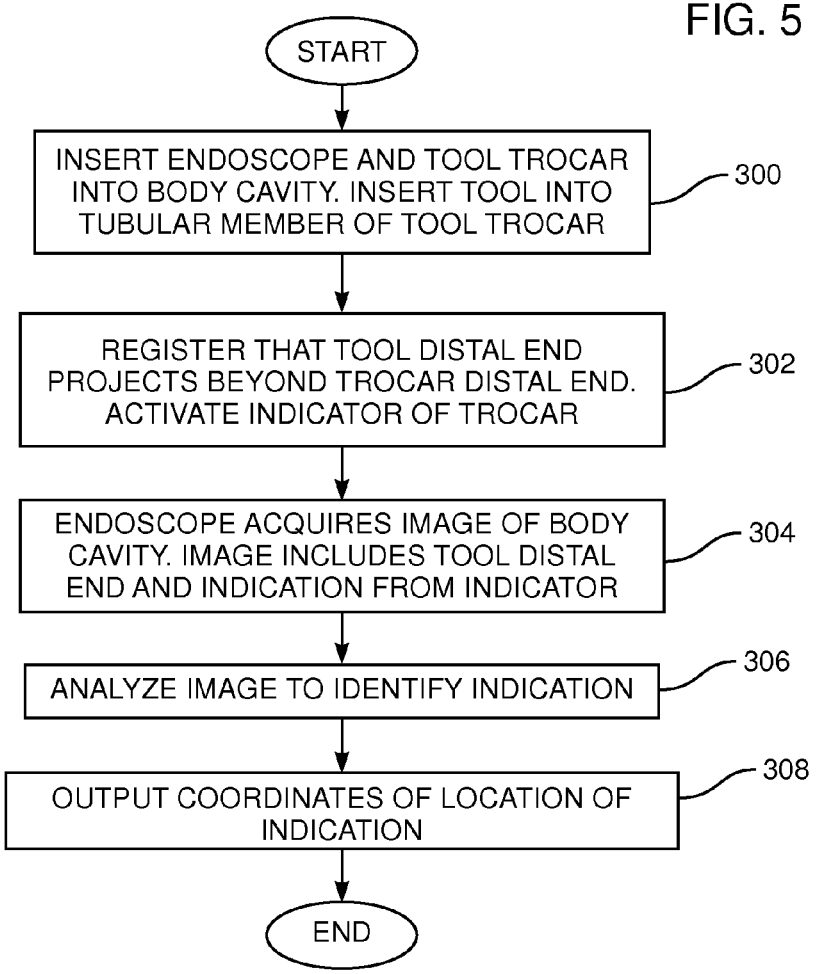
FIG. 5 is a flowchart of steps performed in use of a trocar, according to an embodiment of the present invention.

An embodiment of the present invention provides a trocar which is able to automatically track the location of a distal end of a tool. The tracking is performed after the distal end has been introduced into a region, herein assumed to comprise a body cavity, via the trocar, so as to project beyond the distal end of the trocar. An endoscope may be introduced into the body cavity, and acquires an image of the body cavity and the tool distal end. The endoscope forms the image by radiating "endoscope" light, typically white light, from the endoscope.

In order to provide the automatic tracking, an indicator is formed in a tubular member of the trocar. Typically, within the scene of the endoscope's field of view, the indicator operates to delineate the tool distal end location, by enabling the tool distal end to be distinguished from elements of the body cavity.

In one embodiment, the indicator is an illuminator which radiates light, typically but not necessarily within the visible spectrum, onto the tool distal end when it projects beyond the trocar distal end. The illuminator light is typically selected to have a different spectrum from the spectrum of the endoscope light returning from the body cavity. A processor analyzes the endoscope image, and determines a location of the tool distal end using the differences in spectra of the light from the tool distal end and from the body cavity.

In an alternative embodiment, the indicator is an applicator disposed on the tubular member of the trocar. The applicator may be configured to apply a liquid to the tool as the tool enters the body cavity. The liquid is selected to be quick-drying, so that it forms a solid on the tool distal end. In addition, the solidified liquid is colored to have a spectrum, when illuminated by the endoscope light, that allows it to be easily distinguished from the body cavity. As for the embodiment described above, a processor analyzes the endoscope image and determines a location of the tool distal end using the differences in spectra.

Alternatively, the applicator may be configured as a label dispenser, which applies a label to the tool distal end as the tool enters the body cavity. The label is colored so that, when illuminated by the endoscope light, it has a spectrum that is different from the body cavity spectrum. Alternatively or additionally, the label may have a predefined shape. The processor analyzes the endoscope image to find the label (and thus the tool distal end), using either the differences in spectra or by looking for the predefined shape.

DETAILED DESCRIPTION

Reference is now made to FIG. 1A, which is a schematic illustration of an automated tool tracking system 10, according to an embodiment of the present invention. System 10 may be used in an invasive medical procedure, typically a minimally invasive procedure, on a body cavity 12 of a patient in order to track the location of a tool in the body cavity. By way of example, in the present description the body cavity is assumed to be the abdomen of a patient, and body cavity 12 is also referred to herein as abdomen 12. However, it will be understood that system 10 may be used on substantially any body cavity, such as the bladder or the chest.

System 10 is controlled by an endoscope module 22, comprising a processor 16 communicating with a memory 18. Endoscope module 22 also controls the operation of an endoscope 32. In addition, endoscope module 22 comprises a tool tracker module 20, which is implemented in software within the endoscope module. The tool tracker module uses processor 16 and memory 18 in order to perform its functions, described below.

Typically, module 20 comprises a video object tracker which is configured to receive a video signal from the endoscope system. Module 20 is configured to be aware of the characteristics of an indication used, as described in more detail below, in system 10. The characteristics include, for example, a type and a setting of the indication. For example, if the indication comprises a label the characteristics typically include a label color and a label shape. Tool tracker module 22 is also configured to control, as required, illuminators and/or valves and/or other functional elements of a trocar, as described in more detail below. The configuration of module 20 may be via wireless transmission or through manual input by an operator of system 10.

Endoscope module 22 may also comprise other modules, such as a cavity illumination module, an image processing module, and a zoom/pan module, which may be used by processor 16. The processor uses software stored in memory 18, in the form of the modules referred to above as well as in other forms, to operate system 10. Results of the operations performed by processor 16 may be presented to a medical physician operating system 10 on a screen 24, which typically displays an image of body cavity 12 undergoing the procedure, and/or a graphic user interface to the physician. The software may be downloaded to processor 16 in electronic form, over a network, for example, or it may, alternatively or additionally, be provided and/or stored on non-transitory tangible media, such as magnetic, optical, or electronic memory.

To perform a procedure, the physician inserts trocars into abdomen 12 to penetrate an abdomen wall 26. Herein, the physician is assumed to insert a first trocar 28 and a second trocar 30. Once inserted, the physician is able to pass items required for the procedure through respective tubular members of the trocars into abdomen 12. Thus, endoscope 32 may be passed through a tubular member 34 of trocar 28. Endoscope module 22 provides illumination for the endoscope and displays an image acquired by the endoscope on screen 24. The physician typically uses the endoscope to view the interior of abdomen 12.

Trocar 30 has a tubular member 36, and the physician passes a tool 40 through the tubular member so that it enters body cavity 12. Trocar 30 is operated by tool tracker module 20, and the structure of the trocar, and its functioning as tools such as tool 40 are passed via member 36 into and out of cavity 12, are described with respect to FIGS. 2A and 2B below.

FIG. 1B is a schematic illustration of an automated tool tracking system 11, according to an embodiment of the present invention. Apart from the differences described below, the operation of system 11 is generally similar to that of system (FIG. 1B), and elements indicated by the same reference numerals in both systems are generally similar in construction and in operation. In contrast to system 10, in system 11 tool tracker module 20 is implemented in hardware, typically as a stand-alone hardware unit external to endoscope module 22. While the tool tracker module is configured to communicate and utilize processor 16, having the tool tracker module as a stand-alone hardware unit allows it to be used with existing endoscope modules.

FIGS. 2A and 2B are schematic cross-sectional illustrations of trocar 30, according to a first embodiment of the present invention. FIG. 2A illustrates the trocar before tool 40 passes through tubular member 36 of the trocar. FIG. 2B illustrates the trocar while the tool is passing through tubular member 36, and when a distal end 42 of tool 40 projects beyond a distal end 44 of the trocar. By way of example, in the description herein tubular member is assumed to be cylindrical, with an axis of symmetry 37. Optical elements (described in more detail below) that are located at the distal end of trocar 30 are connected to, and controlled by, tool tracker module 20. For clarity, the connections, typically comprising optical and/or conductive cables, are not shown in the figures. In some embodiments at least some of the connections may comprise wireless connections.

At its distal end 44, trocar 30 comprises at least one illuminator 46 emitting radiation beyond the distal end of the tubular member. If more than one illuminator is used, the illuminators are generally similar in radiative properties. In the description herein, for clarity, different illuminators 46 are identified by appending a letter to the identifying numeral 46 but are referred to collectively as illuminators 46.

By way of example, trocar 30 is assumed to have a first illuminator 46A and a second illuminator 46B located at distal end 44. The two illuminators are inset into a wall 48 of tubular member 36, and are located on opposite sides of a passageway 50 of the tubular member. Illuminators 46A and 46B are typically positioned and inset into wall 48 so that together they project a generally conical pattern of radiation from distal end 44.

However, other numbers and distributions of illuminators 46 may be used in distal end 44, and an optimal number and distribution of illuminators 46 may be determined by one of ordinary skill in the art, without undue experimentation, in order to project the generally conical radiation pattern. However many illuminators are used, they are configured so that the part of tool 40 illuminated (described below) is visible to endoscope 32, typically regardless of the relative orientation and displacement of the tool and the endoscope.

Illuminators 46 may comprise elements which generate the radiation emitted themselves; for example, the illuminators may comprise light emitting diodes (LEDs). Alternatively or additionally, illuminators 46 may be formed as the distal ends of optic fibers which receive the radiation from respective emitters at the proximal ends of the fibers. In this case the emitters may be LEDs or other radiation sources such as incandescent or fluorescent radiators, or lasers.

As described in more detail below, the radiation emitted by illuminators 46 enables tool 40 to be automatically tracked in the image generated by endoscope 32 (FIGS. 1A, 1B). Illuminators 46 thus act as an indicator for the presence of the tool distal end when it projects beyond distal end 44 of the trocar. Typically, endoscope 32 has its own illuminator (not shown in FIGS. 1A, 1B), that is controlled by endoscope module 22. The light emitted by the endoscope illuminator, herein termed "endoscope light," is typically white light. The endoscope light enables the endoscope to acquire an image of tissue of wall 26, such as arteries, veins, and/or other components of the wall. Under the endoscope light the tissue spectrum, corresponding to the color of the imaged tissue, is dependent on the absorption of the endoscope light by the tissue. The tissue spectrum typically comprises varying shades of red.

In embodiments of the present invention the spectrum of the radiation emitted by illuminators 46, herein termed the illumination spectrum, is selected so that tool 40, when illuminated by the radiation, has good visibility with respect to the tissue spectrum. In other words, there is a significant difference between the two spectra. For example, assuming the tissue spectrum has predominating red wavelengths of approximately 650 nm, the illumination spectrum may be selected to have predominant wavelengths for orange (approximately 600 nm), green (approximately 550 nm), blue (approximately 450 nm), or a color having more than one predominant wavelength, such as purple. For simplicity, in the description herein the illumination spectrum is assumed to comprise visible radiation, and is also herein termed light. However, apart from having the significant difference referred to above, there is no limitation on the spectrum emitted by illuminators, so that, for example, the illumination spectrum may comprise infra-red and/or ultra-violet radiation.

Typically, a sensor 52 is located in tubular member wall 48, at distal end 44, the sensor serving to activate illuminators 46 on entry of tool 40 via passageway 50 into distal end 44, and to deactivate the illuminators when the tool is no longer in the passageway. The sensor may be in any convenient form known in the art. For example, the sensor may be a mechanical switch, or alternatively it may be a photoelectric switch.

The description above refers to one trocar 30 configured for automated tool tracking. Embodiments of the present invention also comprise multiple trocars, generally similar to trocar 30, being used simultaneously, so that at any given instance two or more tools may be present in a given body cavity. In the case of multiple trocars, the illumination from each trocar is set to be distinguishable.

The distinguishing feature of the illumination may comprise configuring each illuminator to have a different illumination spectrum, corresponding to wavelength multiplexing. For example, if three trocars are used the respective illuminators may be predominantly orange, green, and blue. Alternatively, the illumination may be time multiplexed, i.e., illuminators 46 may be pulsed. Further alternatively, the endoscope light may be included in the time multiplexing, and this type of time multiplexing could be used to enhance the visibility of the tool when only one trocar is used. Yet further alternatively, a combination of wavelength and time multiplexing may be used to differentiate or distinguish the illumination from multiple trocars.

FIGS. 3A and 3B are schematic cross-sectional illustrations of a trocar 130, according to a second embodiment of the present invention. Apart from the differences described below, the operation of trocar 130 is generally similar to that of trocar 30 (FIGS. 1, 2A and 2B), and elements indicated by the same reference numerals in both trocars 30 and 130 are generally similar in construction and in operation. FIG. 3A illustrates trocar 130 before tool 40 passes through tubular member 36 of the trocar. FIG. 3B illustrates trocar 130 while the tool is passing through tubular member 36, and when distal end 42 of tool 40 projects beyond distal end 44 of the trocar.

In contrast to trocar 30, trocar 130 does not have illuminators 46 to act as an indicator. Rather, distal end 44 of trocar 130 comprises one or more generally similar tubes 132 within wall 48, the tubes exiting from the wall at respective tube openings 134. Openings 134 are located, so that as measured along axis 37 of member 36, the openings are proximal with respect to sensor 52. By way of example, in the present description there are assumed to be two tubes 132, located approximately on opposite sides of passageway 50. Typically, before tube openings 134 there are respective open/close valves 136. Processor 16 sets valves 136 to be open or closed in response to a signal from sensor 52.

However many tubes 132 are used, they are configured so that at least some of the markers (described below) from the openings that are applied to the tool are visible to endoscope 32, typically regardless of the relative orientation and displacement of the tool and the endoscope.

Prior to insertion of tool 40 into trocar 130, valves 136 are closed, and tubes 132 are filled with a liquid. The liquid is selected to be a fast-drying liquid, i.e., a liquid which on exposure to the atmosphere becomes solid, and so is able to act as a marker 138 of the tool upon which it has been deposited. In addition, the liquid is selected so that the marker produced on drying has a marker spectrum which allows the marker, under illumination from the endoscope light, to have good visibility with respect to the tissue of wall 26. In other words, there is a significant difference between the marker spectrum and the tissue spectrum (as exemplified above for the illumination and tissue spectra in the description of trocar 30).

On insertion of tool 40 into trocar 130, so that the distal end of the tool passes sensor 52 and projects beyond the distal end of the trocar, the sensor generates a signal. In response to the signal, processor 16 opens valves 136, so that the liquid in tubes 132 is deposited on the distal end of the tool. Tubes 132 thus act as applicators of the liquid, and the tubes may also be referred to herein as applicators 132. The liquid dries on the tool, forming marker 138. In the embodiment described herein, wherein there are two applicators 132, marker 138 is in two sections. Typically, openings 134 and the amount of liquid stored in applicators 132 are configured so that at least part of marker 138 is visible from any direction with respect to distal end 42 of the tool.

FIGS. 3C and 3D are schematic cross-sectional illustrations of a trocar 150, according to a third embodiment of the present invention. Apart from the differences described below, the operation of trocar 150 is generally similar to that of trocar 130, as described above, and elements indicated by the same reference numerals in both trocars 130 and 150 are generally similar in construction and in operation. FIG. 3C illustrates trocar 150 before tool 40 passes through tubular member 36 of the trocar, and FIG. 3D illustrates the trocar and the tool after distal end 42 of the trocar has passed sensor 52.

In contrast to its location in trocar 130, in trocar 150 sensor 52 is located approximately at the same distal position, i.e., at the same location measured with respect to axis 37 of the trocar, as openings 134. The change of location of the sensor means that markers 138 are located in different positions for trocars 130 and 150: for trocar 130 markers 138 are located on tool 40 more proximally than their location for trocar 150.

FIGS. 3E and 3F are schematic cross-sectional illustrations of a trocar 170, according to a fourth embodiment of the present invention. Apart from the differences described below, the operation of trocar 170 is generally similar to that of trocar 150, and elements indicated by the same reference numerals in trocars 150 and 170 are generally similar in construction and in operation. FIG. 3E illustrates trocar 170 before tool 40 passes through tubular member 36 of the trocar, and FIG. 3F illustrates the trocar and the tool after distal end 42 of the trocar has passed sensor 52.

In trocar 170, rather than locating valves 136 in wall 48, the valves are located outside the wall. Typically, as illustrated in FIGS. 3E and 3F, valves 136 are located in proximity to a proximal end of trocar 170, so that the valves are outside cavity 12.

FIGS. 4A and 4B are schematic cross-sectional illustrations of a trocar 230, according to a fifth embodiment of the present invention. Apart from the differences described below, the operation of trocar 230 is generally similar to that of trocar 30 (FIGS. 1, 2A and 2B), and elements indicated by the same reference numerals in both trocars 30 and 230 are generally similar in construction and in operation. FIG. 4A illustrates trocar 230 before tool 40 passes through tubular member 36 of the trocar, and FIG. 4B illustrates the trocar and the tool after distal end 42 of the trocar has passed sensor 52.

In contrast to trocar 30, trocar 230 does not have illuminators 46, but rather has one or more applicators 232 configured as label dispensers, and also referred to herein as label dispensers 232. Herein, by way of example, there are assumed to be two label dispensers located on opposite sides of passageway 50.

However many label dispensers are used, they are configured so that at least some of the labels (described below) from the dispensers that are deposited on the tool are visible to endoscope 32, typically regardless of the relative orientation and displacement of the tool and the endoscope.

The label dispensers are activated, generally as described above for valves 136, by a signal from sensor 52. When activated each label dispenser 232 deposits a respective label 234 on the distal end of tool 40. As for marker 138, labels 234 are colored or dyed to have a label spectrum that, under illumination from the endoscope light, is easily distinguished from the tissue spectrum of wall 26. Alternatively or additionally, the labels have a predefined shape, such as being circular or rectangular, that is identifiable by processor 16 in the image produced by the endoscope. The labels typically have a fast drying adhesive that is able to cement the labels to the tool within the conditions provided by body cavity 12, for the length of time of the procedure being performed.

Labels 234 may be permanent or removable. Typically, if tool 40 is a disposable tool, then labels 234 may be formed to be permanent. If tool 40 is to be reused, i.e., the tool is not considered as disposable, then labels 234 may be configured as removable labels. In one embodiment the label adhesive is resistant to body temperature conditions, but is soluble in hot water. In an alternative embodiment, the labels are removed on sterilization by autoclaving of the tool, the high temperature of the autoclaving causing the label adhesive to melt. Use of such a label, i.e., one requiring sterilization for removal, acts as a check that sterilization has been performed, i.e., a tool with a label has not been sterilized.

Alternatively, in some embodiments respective label removers 236 may be incorporated in distal end 44, removers 236 being configured to physically remove labels 234 when tool is withdrawn via tubular member 36 from cavity 12.

Processor 16 may be configured to activate label removers 236 in response to a signal from sensor 52 indicating that distal end 42 is not occupying a section of passageway 50 in proximity to the sensor.

FIGS. 4C and 4D are schematic cross-sectional illustrations of a trocar 250, according to a sixth embodiment of the present invention. Apart from the differences described below, the operation of trocar 250 is generally similar to that of trocar 230, and elements indicated by the same reference numerals in both trocars 230 and 250 are generally similar in construction and in operation. FIG. 4C illustrates trocar 250 before tool 40 passes through tubular member 36 of the trocar, and FIG. 4D illustrates the trocar and the tool after distal end 42 of the trocar has passed sensor 52.

In trocar 250 sensor 52 is located approximately at the same distal position, i.e., at the same location measured with respect to axis 37 of the trocar, as label dispensers 232. The change of location of the sensor means that labels 234 are located in different positions for trocars 230 and 250. As illustrated in the figures, for trocar 230 labels 234 are located on tool 40 more proximally than their location for trocar 250.

Figure 6:
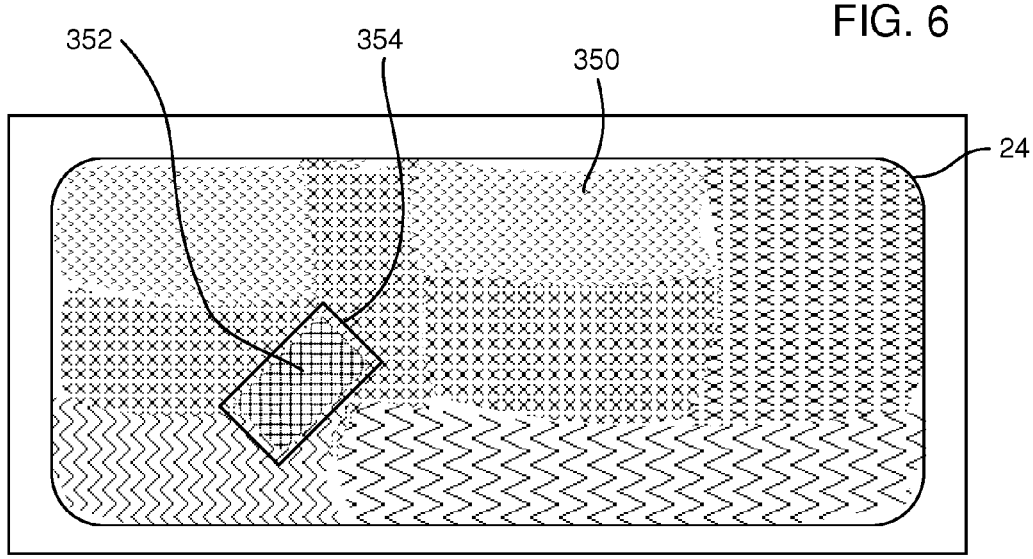
FIG. 6 is a schematic illustration of results of performing the flowchart steps, according to an embodiment of the present invention.

FIG. 5 is a flowchart of steps performed in use of a trocar, and FIG. 6 is a schematic illustration of results of performing the flowchart steps, according to embodiments of the present invention. For clarity, the description of the flowchart assumes, except where otherwise stated, that tool 40 is inserted into body cavity 12 via trocar 30 (FIGS. 1A, 1B). Those having ordinary skill in the art will be able to adapt the description, mutatis mutandis, for one or more other trocars implemented according to the principles of the present invention, such as trocars 130 and 230.

In an initial step 300 of the flowchart, endoscope 32 is inserted into body cavity 12 via trocar 28. Trocar 30 is then inserted into the body cavity, and tool 40 is inserted into tubular member 36 of trocar 30.

In an activate indicator step 302, sensor 52 registers that the tool has passed the sensor, so that tool distal end 42 projects beyond trocar distal end 44, and the sensor transfers a corresponding signal to processor 16. The processor activates illuminators 46, to act as indicators of the location of tool 40 by illuminating the tool. For trocar 130, the processor activates valves 136 so that liquid flows through openings 134, the dried liquid on tool 40 acting as an indication of the tool location. For trocar 230, the processor activates label dispensers 232 to apply labels 234 to tool 40, the labels acting as an indication of the tool location.

In an imaging step 304, endoscope 32 acquires an image 350 of tissue of body cavity 12 (FIG. 6), using the endoscope light to illuminate the cavity. Assuming distal end 42 of tool is in the field of view of the endoscope, the acquired image includes an image of the distal end. The acquired image also includes an indication 352 of the distal end location provided by the indicators described above. Thus, for trocar 30, the indication comprises illumination spectrum light reflected or diffused from the surface of distal end 42 of the tool. For trocar 130 the indication comprises endoscope light, after it has been reflected or diffused from the surface of marker 138, and for trocar 230 the indication comprises endoscope light, after it has been reflected or diffused from the surface of labels 234.

In an image analysis step 306, processor 16 analyzes the acquired image to isolate the indication light in the image. The analysis uses the fact that the indication light has significantly different characteristics, i.e., a different spectrum, than the light from the body cavity tissue. Typically the analysis is on a pixel by pixel basis, to identify a group of contiguous pixels having a spectrum corresponding to the expected indication light. In the case of trocar 30 the expected spectrum is that of illuminators 46; for trocars 130 and 230 the expected spectrum is that from marker 138 or labels 234 under illumination by the endoscope light.

In a final, location, step 308, the processor outputs coordinates of the identified group of pixels for further use by system 10 and/or for systems coupled to system 10. As a first example, the processor may mark a location 354 (FIG. 6), corresponding to tool distal end 42, in image 350 formed on display 24. As a second example, the processor may output the coordinates to a robotic system configured to automatically manipulate instruments such as endoscope 32 and trocar 30. Those having ordinary skill in the art will be aware of other uses for the coordinates output by the processor, and all such uses are assumed to be comprised within the scope of the present invention.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Surgical apparatus, comprising:
 a trocar having a tubular member with a tubular member distal end and a tubular member proximal end, configured for insertion into a body cavity, and defining a passageway configured to allow passage of
 a surgical tool comprising a tool proximal end and a tool distal end, from the tubular member proximal end to a position in which the tool distal end projects beyond the tubular member distal end; and
 an indicator mounted on the trocar configured to apply indications onto surgical tools in the passageway, such that the indications can be identified by an endoscope in the body cavity while the tool distal end projects beyond the tubular member distal end.

2. The apparatus according to claim 1, further comprising:
 a sensor for sensing a position of the surgical tool, mounted on the trocar; and
 wherein the indicator indicates the tool distal end based on a signal of the sensor.

3. The apparatus according to claim 1, wherein the indicator is an applicator, disposed on the trocar, configured to apply a marker to the tool.

4. The apparatus according to claim 3, wherein the marker comprises a liquid, configured to dry in response to being applied to the tool.

5. The apparatus according to claim 3, wherein the marker comprises a label, configured to be deposited on the tool.

6. The apparatus according to claim 5, and comprising a label remover disposed in the trocar, configured to remove the label after deposition thereof, and upon withdrawal of the tool from the trocar via the tubular member.

7. The apparatus according to claim 5, wherein the label is configured to be removed from the tool on autoclaving the tool.

8. The apparatus according to claim 1, further comprising:
 a processor, configured to track the tool in response to the indication of the indicator.

* * * * *